US010058680B2

(12) United States Patent
Ogle et al.

(10) Patent No.: US 10,058,680 B2
(45) Date of Patent: Aug. 28, 2018

(54) STEERABLE STYLET (75) Inventors: David Bruce Ogle, Cowan (AU); Matthew J. Partlett, Emu Plains (AU)

(73) Assignee: CathRx Ltd, Homebush Bay (AU)

( * ) Notice: Subject to any disclaimer, the term of this patent is extended or adjusted under 35 U.S.C. 154(b) by 1898 days.

(21) Appl. No.: 12/919,173

(22) PCT Filed: Mar. 19, 2009

(86) PCT No.: PCT/AU2009/000325
§ 371 (c)(1),
(2), (4) Date: Nov. 29, 2010

(87) PCT Pub. No.: WO2009/114908
PCT Pub. Date: Sep. 24, 2009

(65) Prior Publication Data
US 2011/0137309 A1   Jun. 9, 2011

Related U.S. Application Data (60) Provisional application No. 61/038,293, filed on Mar. 20, 2008.

(51) Int. Cl.
*A61M 25/01* (2006.01)
*A61B 18/14* (2006.01)
(Continued)

(52) U.S. Cl.
CPC .... *A61M 25/0105* (2013.01); *A61M 25/0136* (2013.01); *A61M 25/0138* (2013.01);
(Continued)

(58) Field of Classification Search
CPC ...... A61B 2017/0003; A61M 25/0105; A61M 25/0136; A61M 25/0138; A61M 25/0147; A61M 2025/0163
(Continued)

(56) References Cited

U.S. PATENT DOCUMENTS 5,383,852 A   1/1995   Stevens-Wright
6,224,587 B1  5/2001   Gibson
(Continued)

FOREIGN PATENT DOCUMENTS

EP   0609182   4/1997
EP   0839547   9/2003
(Continued)

OTHER PUBLICATIONS

Australian Search Report for Au Application No. 2009225951, dated Mar. 15, 2011.
(Continued)

*Primary Examiner* — Michael Peffley
*Assistant Examiner* — Samantha Good
(74) *Attorney, Agent, or Firm* — TraskBritt (57) ABSTRACT A steerable stylet assembly includes a tubular member defining a passage, the tubular member defining a first bend enhancing region. At least one further bend enhancing region is arranged intermediate the first bend enhancing region and a distal end of the tubular member. A first actuator is received in the passage of the tubular member, a distal end of the first actuator being fast with the tubular member at a first termination so that relative axial movement between the tubular member and the first actuator causes deflection at the first enhancing region. A second actuator is received in the passage of the tubular member, a distal end of the second actuator being fast with the tubular member at a second termination so that relative axial movement between the tubular member and the second actuator causes the distal part of the tubular member to be formed into a desired shape. The assembly includes a control mechanism to control relative axial movement between the tubular member and each of the actuators.

16 Claims, 8 Drawing Sheets

(51) Int. Cl.
*A61B 17/00* (2006.01)
*A61B 18/00* (2006.01)

(52) U.S. Cl.
CPC ..... *A61M 25/0147* (2013.01); *A61B 18/1492* (2013.01); *A61B 2017/003* (2013.01); *A61B 2018/00375* (2013.01); *A61M 2025/0163* (2013.01)

(58) Field of Classification Search
USPC ................................................. 606/41; 12/41
See application file for complete search history.

(56) References Cited

U.S. PATENT DOCUMENTS

| | | |
|---|---|---|
| 8,251,977 B2 | 8/2012 | Partlett |
| 2003/0040684 A1 | 2/2003 | Soukup et al. |
| 2003/0130712 A1 | 7/2003 | Smits et al. |
| 2004/0106897 A1 | 6/2004 | Thomspon et al. |
| 2007/0255299 A1* | 11/2007 | Vakharia et al. ............ 606/170 |

FOREIGN PATENT DOCUMENTS

| | | |
|---|---|---|
| WO | 2005081202 | 9/2005 |
| WO | 2005123169 | 12/2005 |
| WO | 2006012668 | 2/2006 |
| WO | 2008014557 | 2/2008 |

OTHER PUBLICATIONS

International Preliminary Report on Patentability for PCT/AU2009/000325, dated Sep. 21, 2010.
European Examination Report for European Patent Application No. EP09 722 736.7, dated Dec. 20, 2012, 4 pages.
European Search Report for European Patent Application No. EP09 722 736.7, dated Jul. 4, 2011, 6 pages.
Japanese Examination Report for JP Application No. P2011-500012, dated Sep. 25, 2012, 4 pages.
International Search Report and Written Opinion for PCT/AU2009/000325, dated Apr. 21, 2009.
Definition of Axial Motion, http://www.thefreediotionary.com/axial+motion, Retrieved Aug. 4, 2017, 1 page.

* cited by examiner

STEERABLE STYLET

CROSS-REFERENCE TO RELATED APPLICATIONS

This application is a National Stage filing under 35 U.S.C. § 371 of International Application No. PCT/AU2009/000325, filed on Mar. 19, 2009, which claims the benefit of U.S. Provisional Patent Application Ser. No. 61/038,293, filed on Mar. 20, 2008, the disclosures of which are incorporated herein by reference in their entirety.

FIELD

This invention relates, generally, to a catheter and, more particularly, to a steerable stylet assembly for a catheter.

BACKGROUND

Atrial fibrillation is a condition that affects large groups of people, with new patients being diagnosed each year. These patients have a lower quality of life as well as having up to a seven times increase in the likelihood of heart attacks or strokes. Current therapies include drug treatment or defibrillation, both palliative forms of treatment. Over the past few years, a number of research groups have been investigating curative treatment involving ablative techniques using radio frequency (RF), ultrasound, laser or microwave energy, or cryoablation techniques.

Ablation therapy, while being promising, requires complex catheter designs. Such catheters also have to be reasonably thin to be manoeuvred through a patient's vascular system.

A current approach is the use of a catheter in the shape of a lasso that has a number of electrodes used for diagnostic purposes only. The lasso is positioned through the left atrium of the heart in pulmonary veins. As the lasso is round in shape, it surrounds the inside of the vein. Different sizes of catheters are required depending on the size and shape of the ostium.

Naturally, it is not possible to steer a catheter in a lasso shape through the vasculature of the patient and it is necessary to form the lasso at the site of the patient's heart to be treated. It is difficult to steer the catheter through the patient's vasculature and also to form a distal region of the catheter into the required lasso shape.

Steerable catheters have, in the past, made use of a metal strip or shim contained within the distal end of the catheter as a portion of a steering device. One or more pull wires are connected to the metal strip. Manipulation of these pull wires causes deflection of the distal end of the catheter.

Such a design is complex and difficult to manufacture. In particular, the numerous components must be assembled and joined together, typically by hand.

In addition, a catheter lumen often contains a steering device along with other elements such as electrical conductors and/or irrigation conduits. Therefore, space within the lumen is at a premium.

SUMMARY

According to a first aspect of the invention, there is provided a steerable stylet assembly that includes:
an outer tubular member defining a passage, the tubular member defining a first bend enhancing region spaced proximally from a distal end of the tubular member to facilitate deflection of the tubular member, the tubular member further defining at least one further bend enhancing region arranged intermediate the first bend enhancing region and the distal end of the tubular member to facilitate forming a distal part of the tubular member into a desired shape;
a first actuator received in the passage of the tubular member, a distal end of the first actuator being fast with the tubular member at a first termination located proximally of the at least one further bend enhancing region of the tubular member so that relative axial movement between the tubular member and the first actuator causes deflection of the tubular member in the region of the first bend enhancing region;
a second actuator received in the passage of the tubular member, a distal end of the second actuator being fast with the tubular member at a second termination located distally of the at least one further bend enhancing region of the tubular member so that relative axial movement between the tubular member and the second actuator causes the distal part of the tubular member to be formed into the desired shape; and
a control mechanism to which a proximal end of each of the tubular member, the first actuator and the second actuator is connected to control relative axial movement between the tubular member and each of the actuators, the control mechanism including a mounting formation for mounting to a catheter handle.

The at least one further bend enhancing region may be a second bend enhancing region and the tubular member may include a third bend enhancing region arranged intermediate the first bend enhancing region and the second bend enhancing region, the third bend enhancing region being arranged distally of the first termination. The third bend enhancing region may be circumferentially offset with respect to the second bend enhancing region so that, once the distal part of the tubular member has been formed into the desired shape, the distal part of the tubular member is able to be positioned at least partially in a plane arranged transversely to a longitudinal axis of the tubular member.

Each bend enhancing region of the tubular member may comprise a longitudinally extending, cutaway portion formed at a predetermined location along a length of the tubular member. Each bend enhancing region may further include a restraining arrangement defined by the tubular member, the restraining arrangement comprising a structure arranged at the bend enhancing region to retain the actuators substantially within the confines of the tubular member during bending.

The cutaway portion may subtend an angle greater than 180° of a wall of the tubular member to retain a longitudinally extending web or spine of material of the tubular member. Further, the cutaway portion may subtend a greater angle at a distal region of the cutaway portion than at a proximal region of the cutaway portion.

The cutaway portion may have radiused proximal and distal transition regions for stress relief purposes. Preferably, the proximal transition region has a greater radius than the distal transition region.

Each restraining arrangement may comprise a cage structure defined by the tubular member. The cage structure may comprise a plurality of spaced hoops arranged at longitudinally spaced intervals along the tubular member. A length of each hoop may be greater than a spacing between adjacent hoops. The "length" of a hoop is that dimension parallel to a longitudinal axis of the tubular member.

The first actuator may be a further tubular member received in the passage of the outer tubular member, the further tubular member defining a secondary passage. The second actuator may be a solid elongate element, the solid elongate element being received in, and extending through, the secondary passage of the second tubular member.

The outer tubular member may be of a plastics material that is stiff in torsion and the further tubular member may be of a flexible metal material that resists deflecting when the further tubular member and the outer tubular member are displaced axially with respect to each other.

The control mechanism may include a mounting member for mounting to the catheter handle, the mounting member carrying a first part of the mounting formation for mounting to a handle body of the catheter handle. The control mechanism may include a slide member slidably receivable in the mounting member, the slide member carrying a second part of the mounting formation for mounting to a component of the catheter handle that is axially displaceable relative to the catheter body.

Further, the control mechanism may include a rotatable assembly carried by the mounting member so that rotary motion of the rotatable assembly is translated into axial motion of that one of the outer tubular member, the first actuator and the second actuator connected to the rotatable assembly.

The mounting member may define an aperture through which an electrical cable and/or an irrigation conduit of a catheter of which the stylet assembly forms a part can pass.

According to a second aspect of the invention, there is provided a steerable stylet assembly that includes:
  an outer tubular member defining a passage, the tubular member defining a first bend enhancing region spaced proximally from a distal end of the tubular member to facilitate deflection of the tubular member, the tubular member further defining at least two further bend enhancing regions that are arranged intermediate the first bend enhancing region and the distal end of the tubular member to facilitate forming a distal part of the tubular member into a desired shape;
  a first actuator received in the passage of the tubular member, a distal end of the first actuator being fast with the tubular member at a first termination located proximally of the at least two further bend enhancing regions of the tubular member so that relative axial movement between the tubular member and the first actuator causes deflection of the tubular member in the region of the first bend enhancing region; and
  a second actuator received in the passage of the tubular member, a distal end of the second actuator being fast with the tubular member at a second termination located distally of the at least two further bend enhancing regions of the tubular member so that relative axial movement between the tubular member and the second actuator causes the distal part of the tubular member to be formed into the desired shape.

The first actuator may also be tubular and may define a secondary passage through which the second actuator extends.

One of the at least two further bend enhancing regions may be circumferentially offset with respect to at least one other bend enhancing region of the at least two further bend enhancing regions.

The invention extends also to a catheter assembly that includes:
  a handle including a handle body having a proximal end and a distal end;
  an electrode sheath extending from the distal end of the handle body, the electrode sheath defining a lumen; and
  a steerable stylet assembly, as described above, carried by the handle, the control mechanism being mounted to the proximal end of the handle body and the tubular member, with the actuators in the passage of the tubular member extending through the handle body and into the lumen of the electrode sheath to effect deflection of a distal part of the electrode sheath and the formation of the distal part of the electrode sheath into the desired shape.

DETAILED DESCRIPTION OF EXEMPLARY EMBODIMENT

Figure 3:
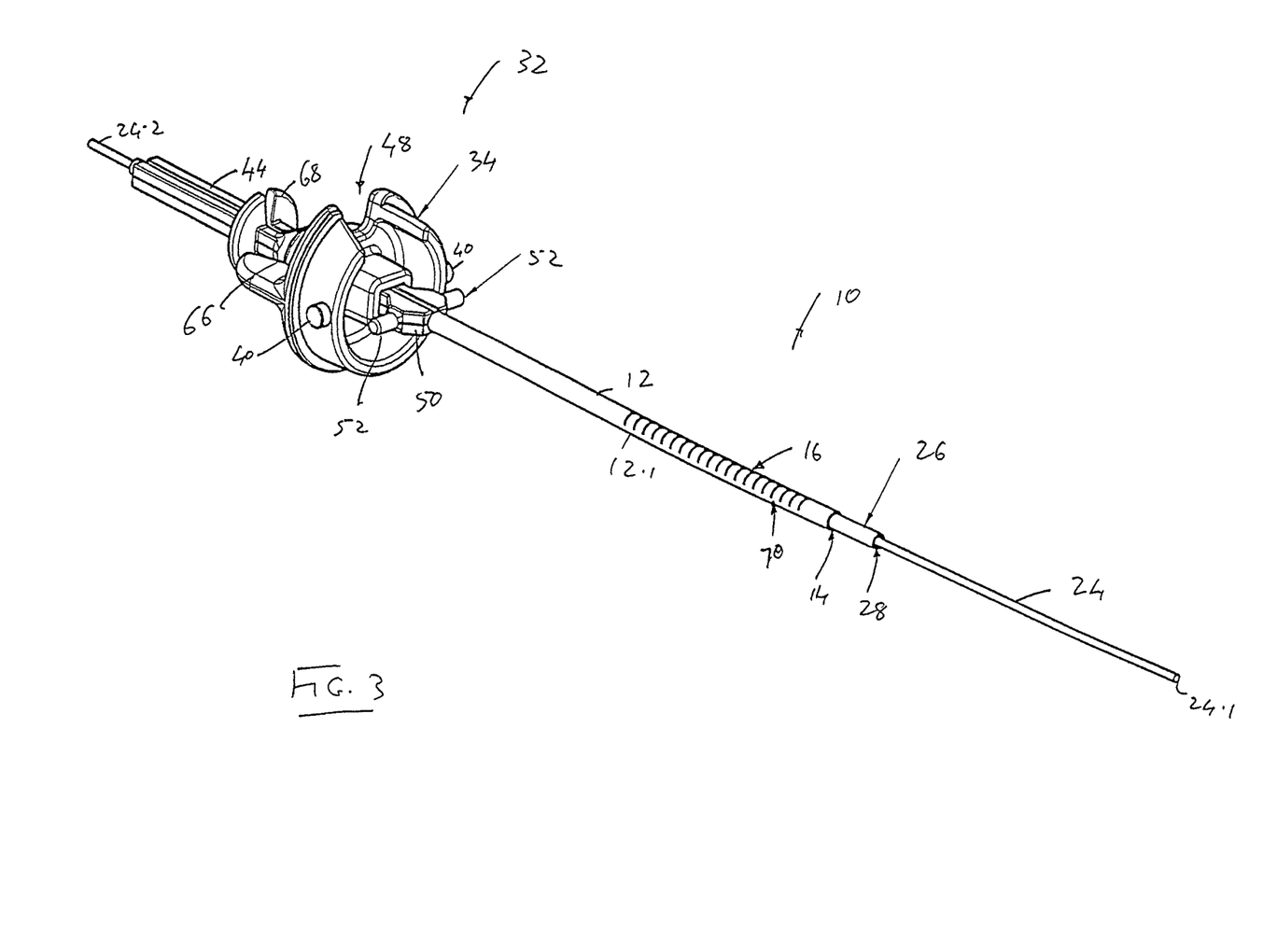
FIG. 3 shows a three-dimensional view of a part of the assembly.

In the drawings, reference numeral 10 generally designates an embodiment of a steerable stylet assembly. The assembly 10 includes an outer tubular member 12 defining a passage 14 (FIG. 3). The outer tubular member 12 defines a first bend enhancing region 16 arranged proximally of a distal end 18 of the tubular member 12.

A second bend enhancing region 20 is arranged intermediate the first bend enhancing region 16 and the distal end 18 of the tubular member 12. Further, a third bend enhancing region 22 is arranged intermediate the first bend enhancing region 16 and the second bend enhancing region 20. The third bend enhancing region 22 is circumferentially offset with respect to the second bend enhancing region 20 as will be described in greater detail below.

Figure 1:
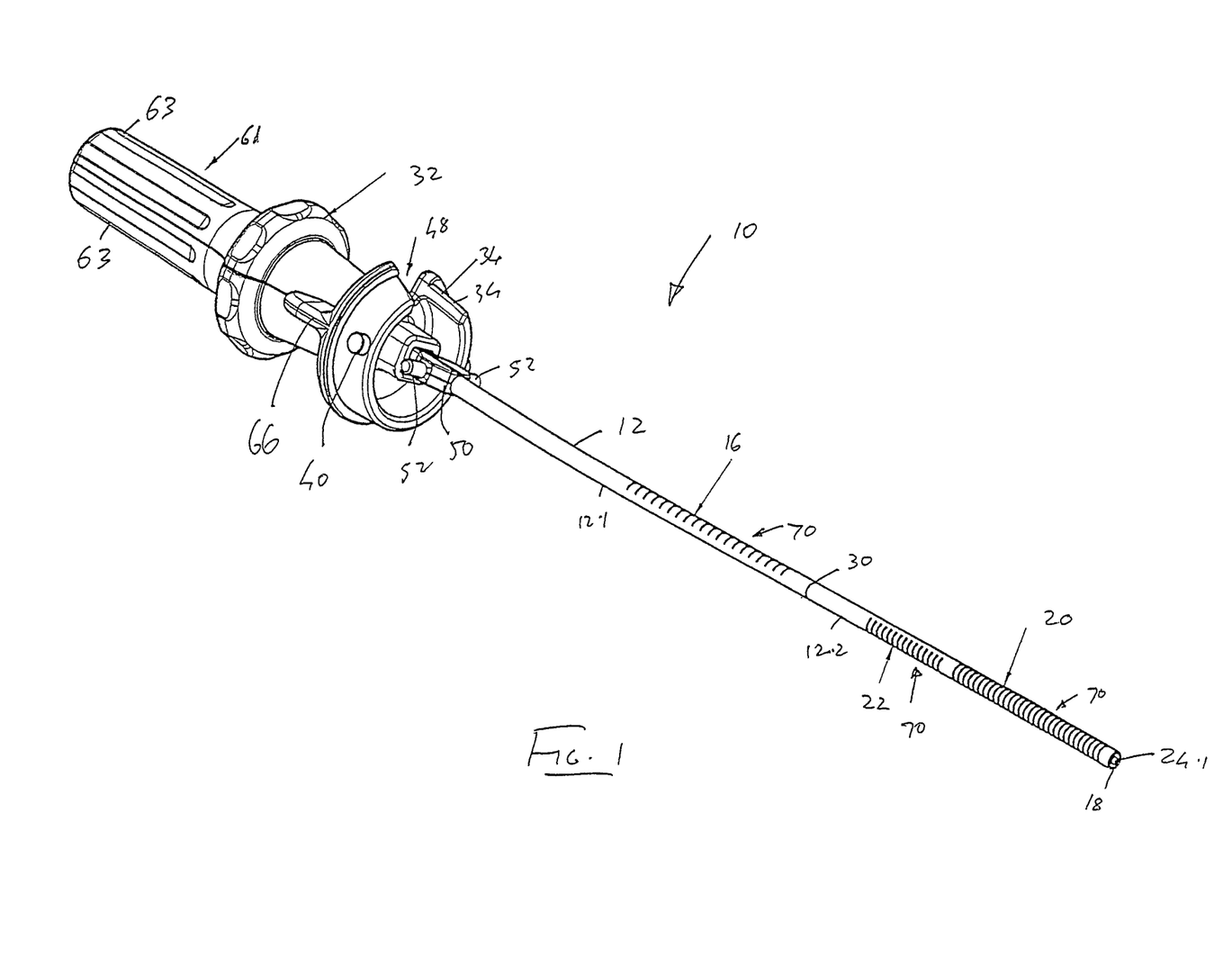
FIG. 1 shows a three-dimensional view of an embodiment of a steerable stylet assembly.

The stylet assembly 10 further includes a first actuator 26. The first actuator 26 is tubular and defines a secondary passage 28, through which a second actuator 24 extends. The first actuator 26 terminates proximally of the bend enhancing region 22 and is fast with the tubular member 12 at a termination 30 (FIG. 1). The termination 30 is arranged intermediate the first bend enhancing region 16 and the third bend enhancing region 22.

The second actuator is in the form of a wire 24. As described above, the second actuator 24 extends through the passage 28 of the first actuator 26 and, thereafter, through the passage 14 of the tubular member 12 and terminates at the distal end 18 of the tubular member 12. A distal end 24.1 of the actuator 24 is fast with the distal end 18 of the tubular member 12.

Figure 5:
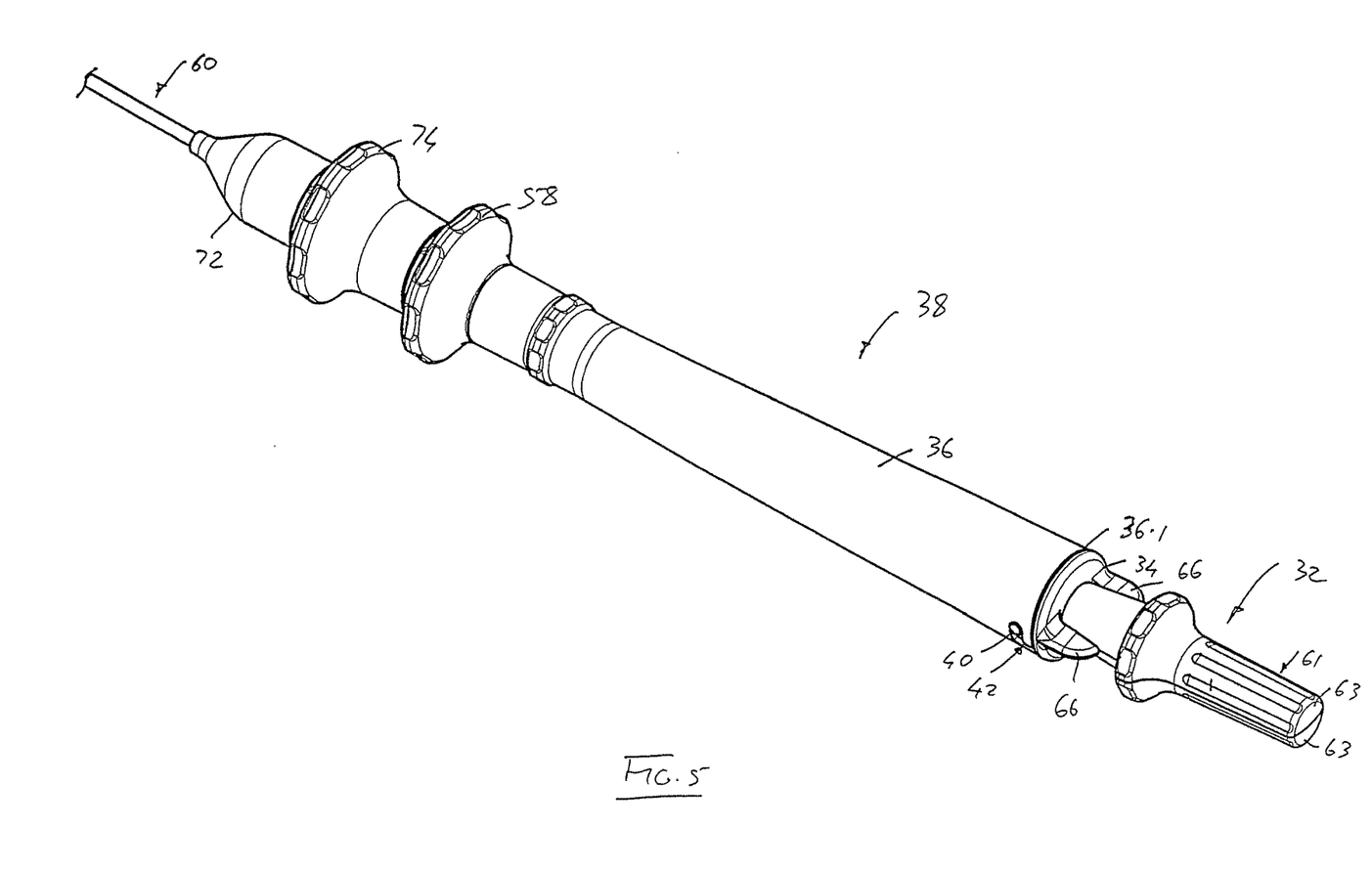
FIG. 5 shows a three-dimensional view of a catheter handle including the steerable stylet assembly.

The stylet assembly 10 includes a control mechanism 32. The control mechanism 32 includes a mounting member in the form of a boss 34. The boss 34 is connectable to a proximal end 36.1 of a handle body 36 of a catheter handle 38 (FIG. 5). The boss 34 carries a first part of a mounting formation of the control mechanism 32 in the form of a pair of opposed lugs 40. The lugs 40 are received, bayonet fashion, in opposed slots 42 at the proximal end 36.1 of the handle body 36 of the catheter handle 38.

As illustrated most clearly in FIG. 3 of the drawings, a stem portion 44 projects proximally from the boss 34. The stem portion 44 supports a screw 46 (FIG. 2), the purpose of which will be described in greater detail below.

The boss 34 further defines an aperture 48 through which an electrical cable and/or an irrigation conduit (neither of which is shown) can pass.

Figure 6:
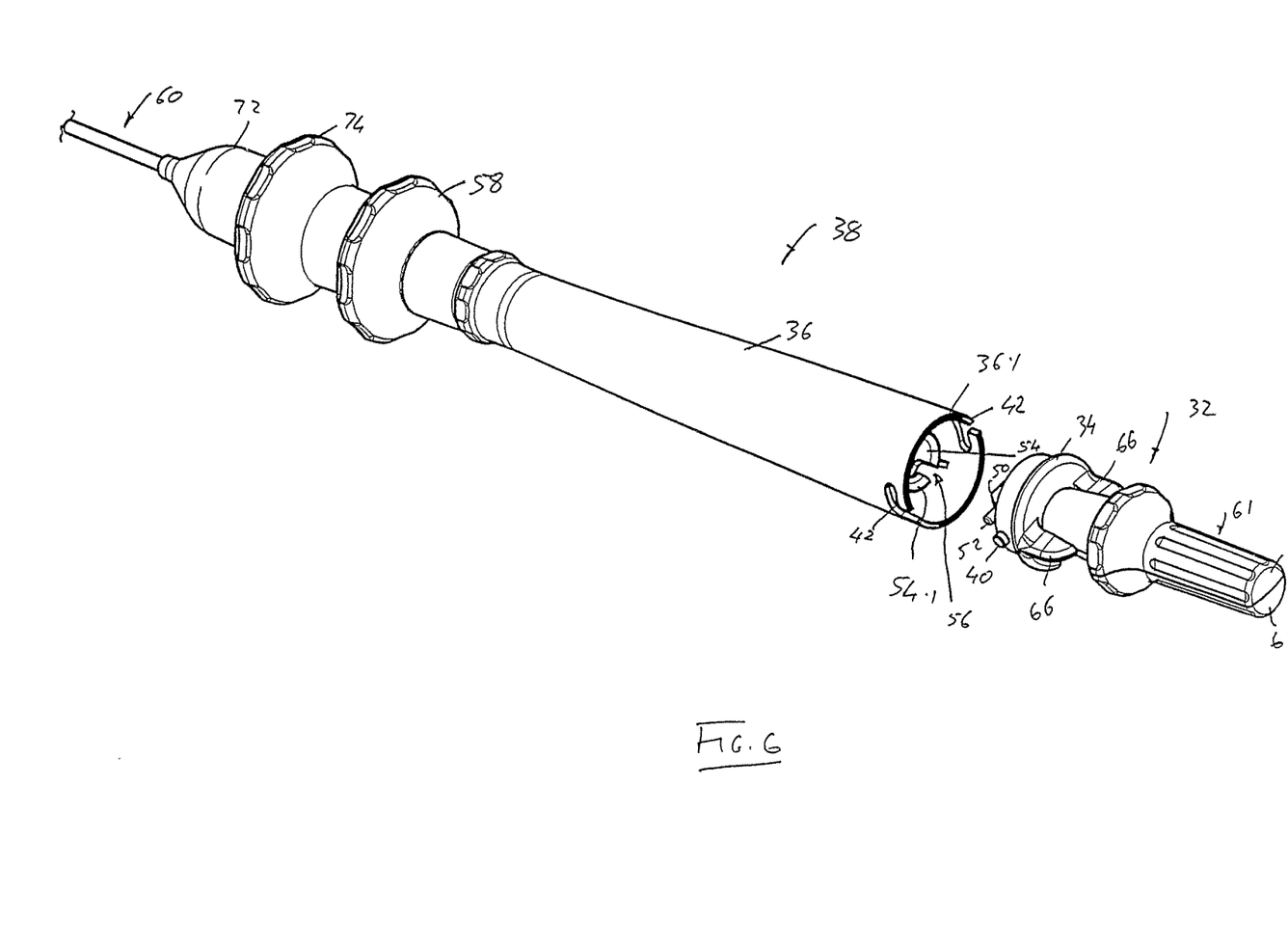
FIG. 6 shows a partially exploded three-dimensional view of the catheter handle including the steerable stylet assembly.

A slide 50 extends from a distal end of the boss 34 and is slidably supported in the boss 34 to be displaceable axially. The slide 50 includes a further part of the mounting formation of the control mechanism 32, the further part being a further pair of opposed lugs 52. These lugs 52 engage a proximal end 54.1 of a shaft 54, which is partially shown in FIG. 6 of the drawings. The lugs 52 are received in a pair of opposed L-shaped slots 56 (one of which is shown in FIG. 6), bayonet fashion. The shaft 54 is fast with a steering control knob 58 carried on the handle body 36 of the catheter handle 38. By axially displacing the steering control knob 58, a distal end of the stylet assembly 10 can be deflected to steer the stylet assembly 10 and, in use, an electrode sheath 60 (FIG. 7) of a catheter assembly 62, as will be described in greater detail below.

A proximal end of the tubular member 12 is fast with the slide 50. Further, a proximal end of the first actuator 26 is fast with the boss 34 of the control mechanism 32. A proximal end 24.2 (FIG. 3) of the second actuator 24 extends through the secondary passage 28 of the first actuator 26 and is fast with the screw 46 as shown most clearly in FIG. 4 of the drawings.

Figure 2:
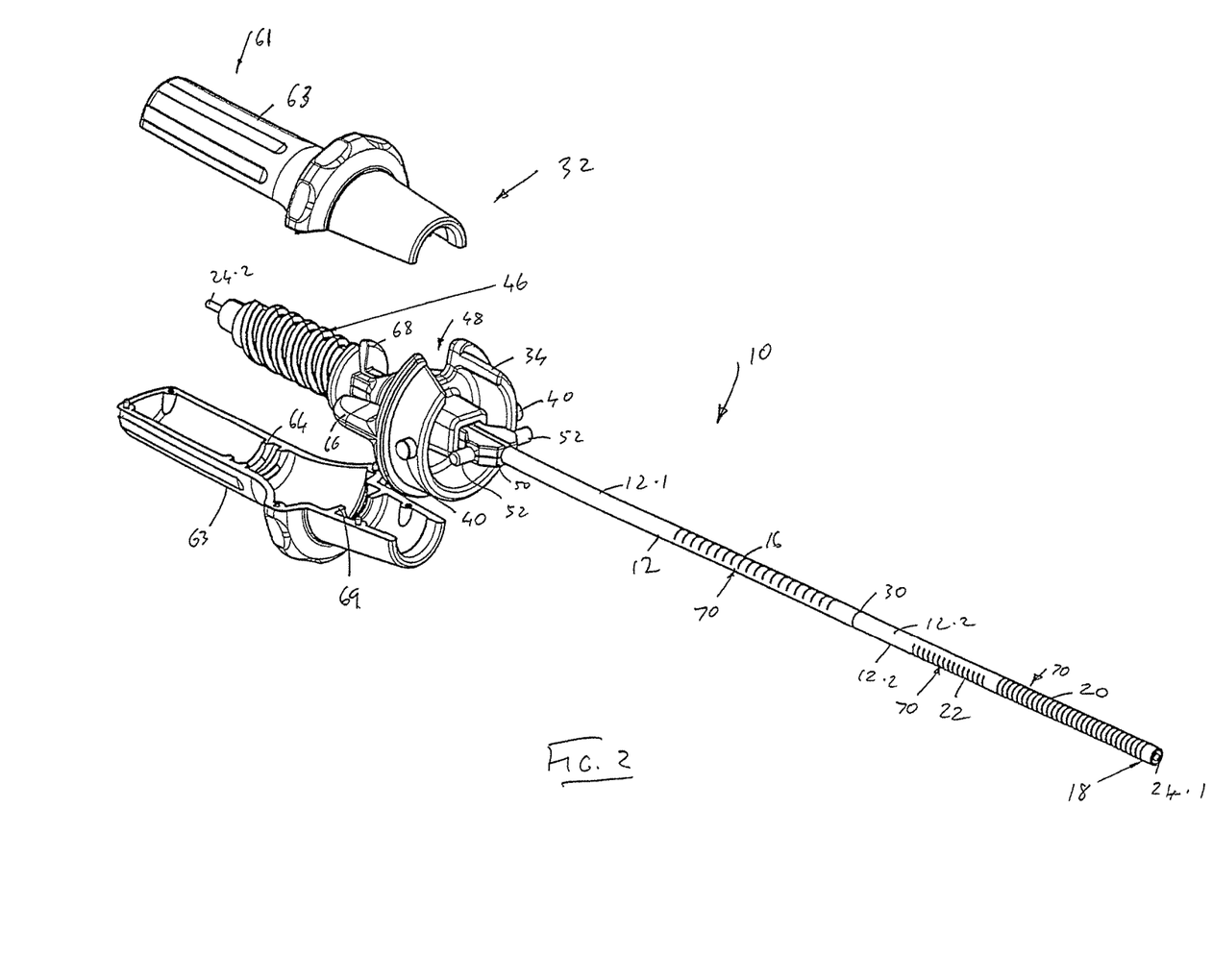
FIG. 2 shows a partially exploded three-dimensional view of the assembly of FIG. 1.

The control mechanism 32 further includes a manipulator 61. The manipulator 61, as shown in FIG. 2 of the drawings, comprises a pair of opposed shells 63 which are secured together about the screw 46. Each shell 63 carriers a threaded portion 64. The threaded portions 64 of the mated shells 63 of the manipulator 61 mesh with the screw 46 of the control mechanism 32. The manipulator 61 and the screw 46 therefore form a rotatable assembly of the control mechanism 32.

Figure 4:
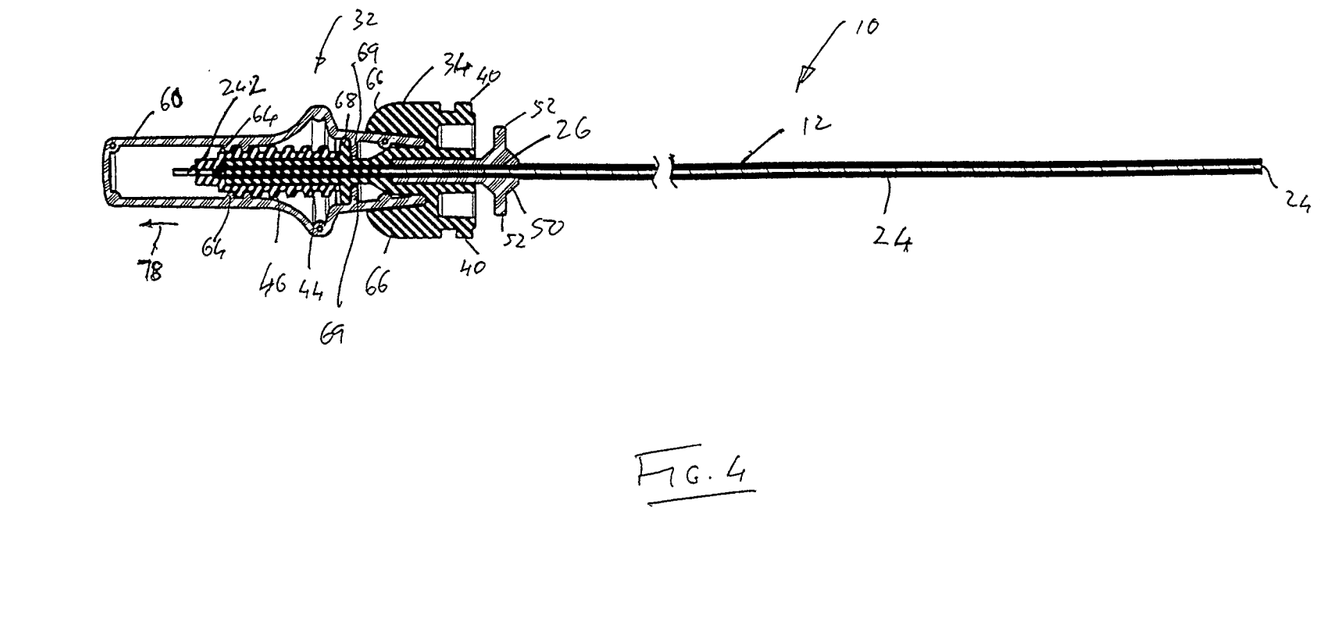
FIG. 4 shows a cross-sectional side view of the part of the assembly of FIG. 3.

A distal end of the manipulator 61 is tapered and is received rotatably between a pair of opposed wings 66 of the boss 34 as shown most clearly in FIG. 4 of the drawings.

The stem portion 44 of the boss 34 carries a collar 68 that supports the manipulator 61 to facilitate rotation of the manipulator 61 relative to the boss 34. Each shell 63 defines a shoulder 69 that bears against the collar 68 and holds the manipulator rotatably fast about the screw 46, as shown most clearly in FIG. 4 of the drawings.

Each bend enhancing region 16, 20 and 22 is as described in the applicant's co-pending applications claiming priority from U.S. Provisional Patent Application Ser. No. 60/861, 642, filed Nov. 28, 2006, and entitled "Catheter Steering System."

Thus, each bend enhancing region 16, 20, 22 includes a cutaway portion subtending an angle greater than 180° of a wall of the tubular member 12. The cutaway portion subtends a greater angle at a distal region of the relevant bend enhancing region 16, 20, 22 than at a proximal region of the relevant bend enhancing region 16, 20, 22. It is to be noted that each bend enhancing region 16, 20, 22 is located a predetermined position along the length of the tubular member 12. The predetermined position of the relevant bend enhancing region 16, 20, 22 is that part of the tubular member 12 at which it is desired that bending is to occur.

Each cutaway portion of the relevant bend enhancing region 16, 20, 22 has a restraining arrangement associated with it. The restraining arrangement is defined by the tubular member 12 and comprises a plurality of longitudinally spaced hoops to form a cage structure 70. The hoops are arranged along the entire length of the relevant bend enhancing region 16, 20, 22 with gaps being defined between the hoops. The arrangement is such that a length of each hoop is greater than the spacing or gap between adjacent hoops. The "length" of each hoop is that dimension parallel to a longitudinal axis of the tubular member 12.

The cutaway portion of each bend enhancing region 16, 20, 22 has radiused proximal and distal transition regions for stress relief purposes. The proximal transition region has a greater radius than the distal transition region. With this arrangement of the transition regions, as well as by having a non-uniform width spine of material due to the differing amounts of material cut away from the proximal region and the distal region of the cutaway portion, more uniform bending of the tubular member 12 is able to be achieved.

The outer tubular member 12 comprises two separate parts, 12.1 and 12.2 joined together at the transition 30. More particularly, the parts 12.1 and 12.2 are adhesively secured together or welded together after a distally located part of the actuator 26 has been made fast with the distal end of the part 12.1 of the tubular member 12.

If desired, the actuator 26 could have a bend enhancing region in register with the bend enhancing region 16 of the part 12.1 of the tubular member 12. The bend enhancing region of the actuator 26 would be of the same configuration as the bend enhancing region 16 of the part 12.1 of the tubular member 12 but with the spines of the bend enhancing regions arranged opposed to each other.

It is not essential that the actuator 26 have a bend enhancing region provided it is of a sufficiently flexible material. For example, the actuator 26 could be a tube of a nickel titanium alloy, or NITINOL™. The actuator 24 is a wire of suitable bio-compatible material such as, for example, stainless steel. The actuator 24 need not be a solid wire but could be a multi-strand cable, if desired.

The outer tubular member 12 is made of a suitable synthetic plastics material such as, for example, PEEK™. This configuration allows sufficient stiffness in torsion so that rotation of the catheter handle 38 about its longitudinal axis is translated into equivalent rotation of the distal end of the electrode sheath 60 of the catheter assembly 62. However, the choice of material still allows deflection or bending of the distal end of the stylet assembly 10 and, hence, the distal end of the electrode sheath 60 of the catheter assembly 62.

The catheter assembly 62 comprises the electrode sheath 60 secured to a distal part 72 of the handle body 36 of the catheter handle 38. The distal part 72 forms part of a projection control mechanism 74. The projection control mechanism 74 is carried on the steering control knob 58 of the catheter handle 36 and is displaceable axially relative to the steering control knob 58. This allows a distal end of the electrode sheath 60 to be displaced axially with respect to the stylet assembly 10.

It is to be noted that a distal end of the electrode sheath 60 carries a plurality of electrodes 76. These electrodes 76 can, by extending the distal end of the electrode sheath 60 with respect to the stylet assembly 10, be brought into contact with tissue in awkward to reach places at a site in a patient's heart or to be steered through restricted structures in the patient's heart.

In use, the electrode sheath 60 of the catheter assembly 62 is inserted into the vasculature of a patient to be treated. Generally, this is done by insertion of the electrode sheath 60 into an introducer (not shown) which, in turn, is inserted into the femoral vein of the patient and the electrode sheath 60 of the catheter assembly 62 is steered through the vasculature of the patient so that a distal end of the electrode sheath 60 is received in the patient's heart. Steering of the electrode sheath 60 is effected by way of the stylet assembly 10 being received in a lumen (not shown) of the electrode sheath 60. Steering is effected by manipulating the tubular member 12 and the actuator 26 with respect to each other. This is done by displacing the steering control knob 58 axially with respect to the handle body 36. It will be appreciated that the tubular member 12 is fast with the slide 50 secured to the steering control knob 58 via the shaft 54. The actuator 26 is fast with the boss 34 and, hence, the handle body 36 of the catheter handle 38. As a result, relative axial movement between the tubular member 12 and the actuator 26 by manipulation of the steering control knob 58 causes bending of the tubular member 12 about the bend enhancing region 16 and facilitates steering of the electrode sheath 60 of the catheter assembly 62 through the vasculature of the patient.

Figure 7:
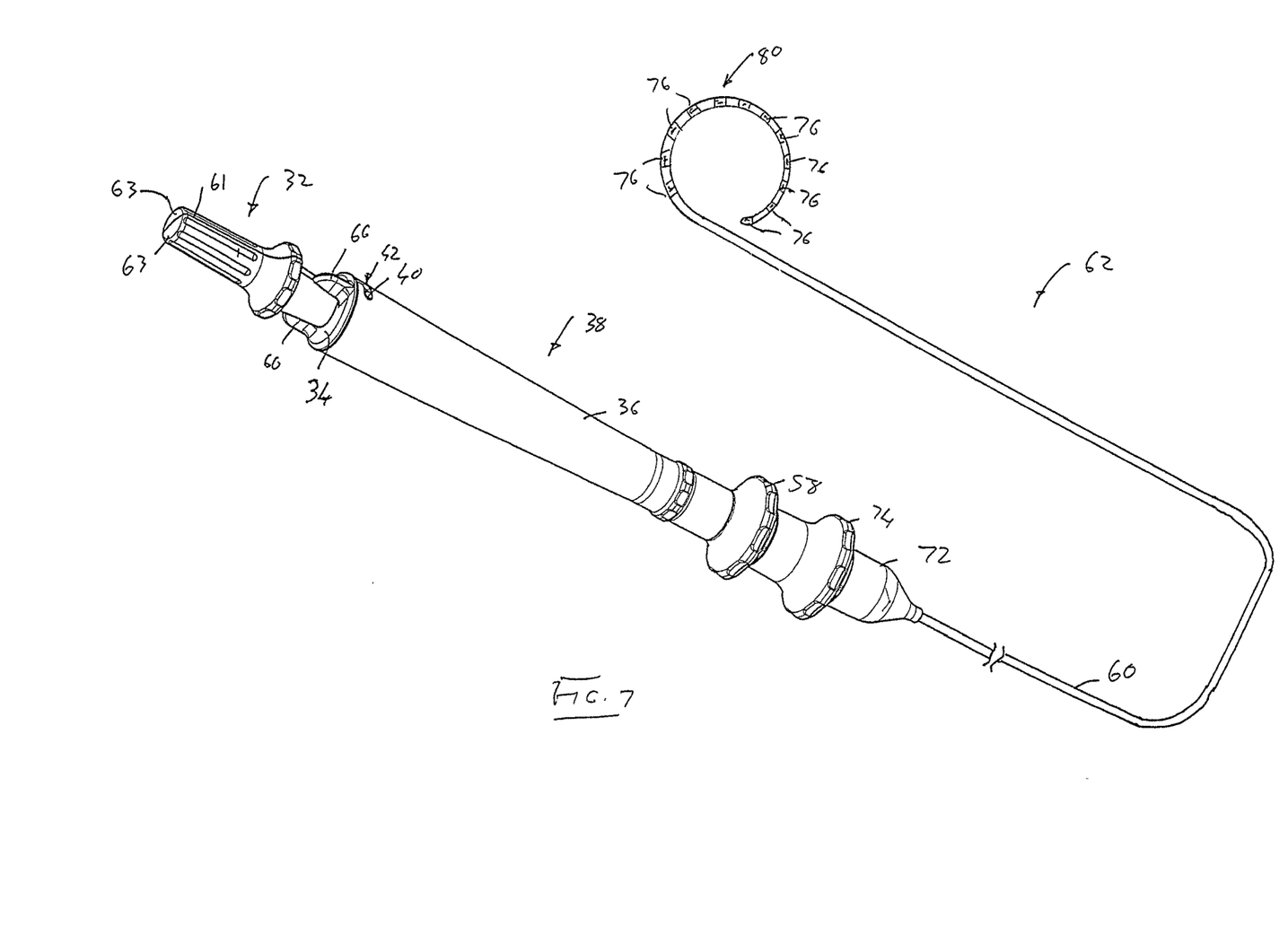
FIG. 7 shows a three-dimensional view of a catheter assembly with an electrode sheath of the catheter assembly in a first orientation.
Figure 8:
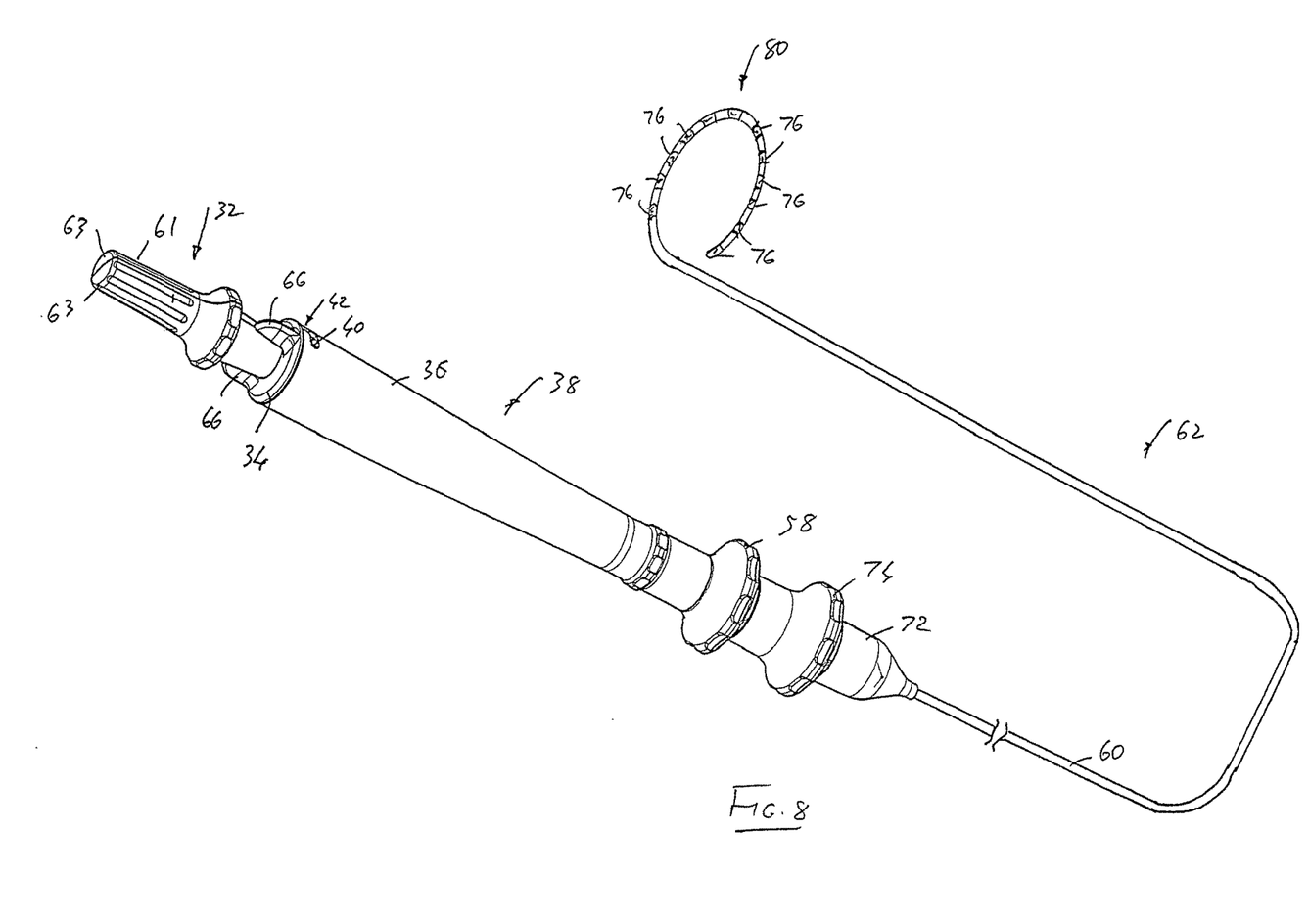
FIG. 8 shows a three-dimensional view of the catheter assembly of FIG. 7 with the electrode sheath of the catheter assembly in a second, operative orientation.

When the distal end of the electrode sheath 60 is at the desired location in the patient's heart, it is required that the distal end is formed into a predetermined shape for diagnostic and/or therapeutic purposes. This is effected by manipulation between the tubular member 12 and the second actuator 24 of the stylet assembly 10. Manipulation between the tubular member 12 and the actuator 24 is controlled by the manipulator 61. When the manipulator 61 is rotated relative to the screw 46, the screw 46 is drawn in the direction of arrow 78 (FIG. 4) causing relative axial displacement between the actuator 24 and the tubular member 12. This causes the distal end of the electrode sheath 60 to form into a loop 80 as shown in FIG. 7 of the drawings due to the stylet assembly bending about the bend enhancing region 20. Further rotation of the manipulator 61 relative to the screw 46 causes the stylet assembly 10 to bend about the bend enhancing region 22. The bend enhancing region 22 is, as described above, circumferentially offset with respect to the bend enhancing region 20. Thus, further manipulation of the manipulator 61 relative to the screw 46 causes the loop 80 to be positioned in a plane which is transverse to a longitudinal axis of the electrode sheath 60 as shown in FIG. 8 of the drawings. In this orientation, the loop 80 can be urged against the relevant site in the patient's body, for example, at the ostium to a pulmonary vein of the patient.

Hence, it is an advantage of the invention that a steerable stylet assembly 10 is provided which is easily manipulable by a clinician and which facilitates steering of a catheter through a patient's vasculature. Thus, it is a reasonably straightforward process for the clinician to steer the distal end of the catheter assembly 62 through the patient's vasculature and, once the distal end of the catheter assembly has been positioned at the desired location in the patient's heart, to form the distal end into the desired shape. In addition, the use of the catheter handle 38 with the control mechanism 32 lends itself to use in a remote control device. Thus, the clinician is able to manipulate the catheter assembly 62 while being remotely positioned and out of radiation fields used in the procedure. This reduces exposure of the clinician to such radiation rendering the system safer to use. Also, the use of a screw mechanism for the control mechanism facilitates more accurate control of loop formation at the distal end of the catheter assembly 62.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

The invention claimed is:

1. A steerable stylet assembly, comprising:
    an outer tubular member comprising a wall and defining a passage, the wall of the outer tubular member defining a first bend enhancing region and at least one further bend enhancing region, the first bend enhancing region spaced proximally from a distal end of the outer tubular member to facilitate deflection of the outer tubular member, the at least one further bend enhancing region arranged intermediate the first bend enhancing region and the distal end of the outer tubular member to facilitate forming a distal part of the outer tubular member into a desired shape, wherein the first bend enhancing region and the at least one further bend enhancing region each comprise a longitudinally extending cutaway portion formed in the wall of the outer tubular member;
    a first actuator received in the passage defined by the outer tubular member, a distal end of the first actuator directly connected to the wall of the outer tubular member at a first termination located proximal to the at least one further bend enhancing region so that relative axial movement between the wall of the outer tubular member and the first actuator causes deflection of the outer tubular member in the region of the first bend enhancing region;
    a second actuator received in the passage defined by the outer tubular member, a distal end of the second actuator being directly connected to the wall of the outer tubular member at a second termination located distal from the at least one further bend enhancing region so that relative axial movement between the wall of the outer tubular member and the second actuator causes the distal part of the outer tubular member to be formed into the desired shape; and
    a control mechanism to which a proximal end of each of the wall of the outer tubular member, the first actuator and the second actuator is connected to control relative axial movement between the wall of the outer tubular member and each of the actuators, the control mechanism including a mounting formation for mounting to a catheter handle.

2. The assembly of claim 1, wherein the at least one further bend enhancing region is a second bend enhancing region and in which the wall of the outer tubular member defines a third bend enhancing region arranged intermediate the first bend enhancing region and the second bend enhancing region, the third bend enhancing region being arranged distal from the first termination.

3. The assembly of claim 2, wherein the third bend enhancing region is circumferentially offset with respect to the second bend enhancing region so that, once the distal part of the outer tubular member has been formed into the desired shape, the distal part of the outer tubular member is configured to be positioned at least partially in a plane arranged transversely to a longitudinal axis of the outer tubular member.

4. The assembly of claim 1, wherein the first bend enhancing region and the at least one further bend enhancing region each further includes an associated restraining arrangement defined by the outer tubular member, the restraining arrangement comprising a structure arranged at the associated one of the first bend enhancing region and the at least one further bend enhancing region to retain the actuators substantially within the confines of the outer tubular member during bending.

5. The assembly of claim 4, wherein each restraining arrangement comprises a cage structure defined by the outer tubular member.

6. The assembly of claim 1, wherein the first actuator is a further tubular member received in the passage of the outer tubular member, the further tubular member defining a secondary passage.

7. The assembly of claim 6, wherein the second actuator is a solid elongate element, the solid elongate element being received in, and extending through, the secondary passage of the further tubular member.

8. The assembly of claim 6, wherein the outer tubular member comprises a plastic material which is stiff in torsion and the further tubular member comprises a flexible metal material which resists deflecting when the further tubular member and the outer tubular member are displaced axially with respect to each other.

9. The assembly of claim 1, wherein a first part of the mounting formation is carried by a mounting member of the control mechanism, the mounting formation configured for mounting to a handle body of the catheter handle.

10. The assembly of claim 9, wherein the control mechanism includes a slide member slidably receivable in the mounting member, the slide member carrying a second part of the mounting formation for mounting to a component of the catheter handle that is axially displaceable relative to the catheter body.

11. The assembly of claim 9, wherein the control mechanism includes a rotatable assembly carried by the mounting member so that rotary motion of the rotatable assembly is translated into axial motion of that one of the outer tubular member, the first actuator and the second actuator connected to the rotatable assembly.

12. The assembly of claim 9, wherein the mounting member defines an aperture sized and configured to allow an electrical cable and/or an irrigation conduit to extend through the aperture.

13. A steerable stylet assembly, comprising:
an outer tubular member comprising a wall and defining a passage, the wall of the outer tubular member defining a first bend enhancing region and at least two further bend enhancing regions, the first bend enhancing region spaced proximally from a distal end of the outer tubular member to facilitate deflection of the outer tubular member, the at least two further bend enhancing regions being arranged intermediate the first bend enhancing region and the distal end of the outer tubular member to facilitate forming a distal part of the outer tubular member into a desired shape, each of the at least two further bend enhancing regions comprising a longitudinally extending cutaway portion formed in the wall of the outer tubular member;
a first actuator received in the passage defined by the outer tubular member, a distal end of the first actuator directly connected to the wall of the outer tubular member at a first termination located proximal to the at least two further bend enhancing regions so that relative axial movement between the wall of the outer tubular member and the first actuator causes deflection of the outer tubular member in the region of the first bend enhancing region; and
a second actuator received in the passage defined by the outer tubular member, a distal end of the second actuator directly connected to the wall of the outer tubular member at a second termination located distal from the at least two further bend enhancing regions so that relative axial movement between the wall of the outer tubular member and the second actuator causes the distal part of the outer tubular member to be formed into the desired shape.

14. A steerable stylet assembly, comprising:
an outer tubular member comprising a wall and defining a passage, the wall of the outer tubular member defining a first bend enhancing region and at least one further bend enhancing region, the first bend enhancing region spaced proximally from a distal end of the outer tubular member to facilitate deflection of the outer tubular member, the at least one further bend enhancing region arranged intermediate the first bend enhancing region and the distal end of the outer tubular member to facilitate forming a distal part of the outer tubular member into a desired shape;
a first actuator received within the passage defined by the outer tubular member and surrounded thereby, the first actuator being tubular and defining a secondary passage, a distal end of the first actuator being fast with the outer tubular member at a first termination located proximal to the at least one further bend enhancing region so that relative axial movement between the wall of the outer tubular member and the first actuator causes deflection of the outer tubular member in the region of the first bend enhancing region; and
a second actuator received within the passage defined by the outer tubular member and surrounded thereby, the second actuator extending through the secondary passage defined by the first actuator, a distal end of the second actuator being fast with the wall of the outer tubular member at a second termination located distal from the at least one further bend enhancing region so that relative axial movement between the wall of the outer tubular member and the second actuator causes the distal part of the outer tubular member to be formed into the desired shape.

15. The assembly of claim 13, wherein one of the at least two further bend enhancing regions is circumferentially offset with respect to at least one other bend enhancing region of the at least two further bend enhancing regions.

16. A catheter assembly, comprising:
a handle including a handle body having a proximal end and a distal end;
an electrode sheath extending from the distal end of the handle body, the electrode sheath defining a lumen; and
a steerable stylet assembly, as claimed in claim 1, carried by the handle, the control mechanism being mounted to the proximal end of the handle body and the outer tubular member, with the actuators in the passage of the outer tubular member extending through the handle body and into the lumen of the electrode sheath to effect deflection of a distal part of the electrode sheath and the formation of the distal part of the electrode sheath into the desired shape.

* * * * *